United States Patent [19]

Elger et al.

[11] Patent Number: 5,795,881
[45] Date of Patent: Aug. 18, 1998

[54] COMBINED USE OF AN ANTIGESTAGEN AND A PROGESTERONE SYNTHESIS INHIBITOR OF THE TRILOSTANE AND EPOSTANE TYPE

[75] Inventors: Walter Elger; Sybille Beier; Beate Kosub; Marianne Faehnrich; Krzysztof Chwalisz; Syed Hamiduddin Hasan, all of Berlin, Germany; Gordon Oliver Potts, North Chatham, N.Y.

[73] Assignee: Schering Aktiengesellschaft, Berlin, Germany

[21] Appl. No.: 385,801

[22] Filed: Feb. 9, 1995

Related U.S. Application Data

[63] Continuation of Ser. No. 69,653, Jun. 1, 1993, abandoned, which is a continuation of Ser. No. 448,477, Dec. 11, 1989, abandoned, which is a continuation-in-part of Ser. No. 206,750, Jun. 15, 1988, abandoned.

[30] Foreign Application Priority Data

Jun. 16, 1987 [DE] Germany ............ P 37 20 420.3

[51] Int. Cl.⁶ ............ A61K 31/56; A61K 31/58
[52] U.S. Cl. ............ 514/170; 514/171; 514/172; 514/179
[58] Field of Search ............ 514/170, 171, 514/172, 179

[56] References Cited

U.S. PATENT DOCUMENTS

| 4,062,954 | 12/1977 | Potts | 424/241 |
| 4,160,027 | 7/1979 | Christiansen | 424/241 |
| 4,626,531 | 12/1986 | Elger et al. | 514/171 |
| 4,670,426 | 6/1987 | Zor et al. | 514/171 |

OTHER PUBLICATIONS

Chemical Abstracts, vol. 101, 1984 ; pp. 80.

Webster's Third New International Dictionary of the English Language, Unabridged, 1976, p. 1246.

"Studies on Interactions of Antiprogestins with Prostaglandins and . . . ", W. Elger et al., Hormone Antagonists for Fertility Reg., 1988, pp. 105–114.

"Effect of Epostane, ZK 98299, and ZK 98734 on the Interruption of . . . ", B.W. Snyder et al., Biol. of Repro., 40, 1989, pp. 549–554.

Physician'Desk Ref., 48th ed., 1994, pp. 539–540, 1072–1074 and 1651.

Primary Examiner—Kimberly Jordan
Attorney, Agent, or Firm—Millen, White, Zelano & Branigan, P.C.

[57] ABSTRACT

A pharmaceutical agent contains a progesterone synthesis inhibitor (ProI) of the trilostane or epostane type and an antigestagen (AG). It can be used for inducing delivery at term in humans and animals, for terminating normal or pathological pregnancies therein or for treatment of hormone-dependent tumors, endometriosis or dysmenorrhea.

31 Claims, 1 Drawing Sheet

COMBINED USE OF AN ANTIGESTAGEN AND A PROGESTERONE SYNTHESIS INHIBITOR OF THE TRILOSTANE AND EPOSTANE TYPE

This is a continuation of the application Ser. No. 08/069,653 filed Jun. 1, 1993, now abandoned, which is a continuation of Ser. No. 07/448,477 filed Dec. 11, 1989, now abandoned; which was a C-I-P of Ser. No. 07/206,750 filed Jun. 15, 1998, also abandoned.

BACKGROUND OF THE INVENTION

This invention relates to a pharmaceutical agent, which comprises a progesterone synthesis inhibitor (ProI) of the type of trilostane and epostane, and an antigestagen (AG).

It is sometimes necessary, in order to avert dangers to the mother and/or child, to induce labor artificially or terminate pregnancy prematurely. Surgical techniques and pharmacological methods are available for this purpose.

One possible pharmacological method is the vaginal or intramuscular administration of prostaglandins, which, in the case of termination of pregnancy, is carried out in the first or second trimester of pregnancy (Contraception 1983, Vol. 27, 51–60 and Int. J. Gynaecol. Obstet. 1982, Vol. 20, 383–386).

The advantage of prostaglandin use is the possibility of employing it over a long period of the pregnancy. Disadvantages of prostaglandins which should be mentioned are acute side effects such as pain and nausea. In addition, in the case of the termination of pregnancy in advanced phases of pregnancy, the success rate does not exceed 90%, even with prolonged duration of prostaglandin treatment.

Another possibility for terminating pregnancy comprises administration of an antigestagen (Med. et Hyg. 1982, Vol. 40, 2087–2093). Antigestagens are better tolerated than are prostaglandins, but are less effective, and have a longer latency period and greater individual variability of the onset of action compared with prostaglandins. In addition, it has been observed clinically that they have a tendency to cause hemorrhages, which can be severe.

Although the conjoint use of prostaglandins and antigestagens (EP 84730108.2) has uncontestable advantages over administration of the individual active substances alone (especially reduction in the amount of each active substance), it does not, for example, solve the problems which generally occur when prostaglandins are used: undesired side effects, such as gastrointestinal effects or uterine pain, the necessity for in-patient treatment, the storage and shelf-life of the pharmaceutical, owing to a lack of stability, being limited and/or elaborate, the impossibility of the most user-friendly administration form, namely oral, and thus the impossibility of combining the two active substances in a tablet, pill or coated tablet.

It has also been suggested to use the combination of prostaglandins, glucocorticoids and antigestagens for the induction of labor or for termination of pregnancy. The antigestagens can be either receptor competitive progesterone antagonists or compounds which antagonize the effect of gestagens by a different route, e.g., the derivatives of trilostane of U.S. Pat. No. 4,160,027. (See U.S. Ser. No. 790,020, filed Oct. 22, 1985; DOS 3438994.6, filed Oct. 22, 1984).

Another possibility which has been suggested for premature termination of pregnancy is treatment with progesterone synthesis inhibitors such as epostane derivatives (also U.S. Pat. No. 4,160,027). However, it has been found that it is impossible to induce abortion in guinea pigs in advanced pregnancy even with doses high enough to cause a marked reduction in the serum progesterone level. In early human pregnancy, the success rate even with the maximum epostane doses is not 100%. Once again, clinical treatment is successful only in combination with prostaglandins, but very large amounts of active substances (30 mg of $PGE_2$, 5×600 mg of epostane) are necessary for this. In addition to this disadvantage, the method is subject to the problems associated with the use of prostaglandins which have been discussed above.

Pharmaceutical compositions for post-coital fertility control, which contain a competitive progesterone antagonist (antigestagen) as well as a progesterone and estrogen synthesis blocker are already generically described in U.S. Pat. No. 4,670,426. Typical representatives of the competitive progesterone antagonists to be used are fluocinolone acetonide, triamcinolone acetonide, steroids with a cyclic 16,17-acetal with acetone and 17β-hydroxy-11β,(4-dimethylaminophenyl-1)-17α-prop-1-ynyl-estra-4,9-dien-3-one and equivalent derivatives. The stated dosages for these compounds is between 20 and 100 mg per person per day. As examples for the progesterone and estrogen synthesis blocker there are cited aminogluthetimide, 2α-cyano-4,4,17α-trimethyl-5-androst-5-ene-17β-ol-3-one, 20,25-diazacholesterol, and compounds with equivalent activity. Doses of 300 to 1000 mg are stated. The use of the agent according to U.S. Pat. No. 4,670,426 has to take place as early as possible within the first week after sexual intercourse over a period of 3 days; the treatment should best be continued 2 to 6 days. Prevention of nidation and thus of a pregnancy is caused by the synergistic effect in the combined use of the two components of the composition, and with a success rate on the order of 90% or more.

More recently the use of antigestagens in the field of tumor therapy, especially for treatment of mastocarcinoma, has also been discussed. A first phase II study with the already mentioned 17β-hydroxy-11β-(4-dimethylaminophenyl)-17α-prop-1-ynyl-estra-4,9-dien-3-one on postmenopausal or ovariectomy endocrine-therapy-resistant patients with metastasizing mastocarcinoma is reported by Maudelonde et al. in Hormonal Manipulation of Cancer, eds. J. G. M. Klijm, R. Paridaens and J. A. Folkens in Raven Press, p. 55 (1987).

SUMMARY OF THE INVENTION

This invention provides agents which do not have the above-mentioned disadvantages, are additionally highly effective, where possible more effective than the known agents, and have fewer side effects than the latter.

This invention has found that the use of a combination of progesterone synthesis inhibitors, especially of the trilostane and epostane type(s), and antigestagens (competitive progesterone antagonists), i.e., of substances which both act on the principle of inhibition of the action of progesterone (and each of which is, by itself, only incompletely effective or entirely ineffective, even at high dosages), is surprisingly completely effective even with a dramatic reduction in these doses.

Thus, this invention relates to a method of inducing labor, terminating pregnancy, treating a hormone-dependent tumor, treating endometriosis, or treating dysmenorrhea, comprising administering a composition comprising effective amounts of a progesterone synthesis inhibitor and an antigestagen.

Progesterone synthesis inhibitors (ProI) especially of the trilostane and epostane type are preferred. ProI and antigestagens (AG) can be administered conjointly for inducing labor, i.e., at term, in humans and animals and for terminating normal or pathological pregnancies therein. Further, the combination according to the invention of progesterone synthesis inhibitors and antigestagen is suitable for treatment of endometriosis, dysmenorrhea and hormone-dependent tumors, for example, carcinoma of the breast and durosarcoma.

A 100% effectiveness is absolutely necessary for the use of these compounds for terminating pregnancy or inducing labor, since an embryotoxic action of the involved compounds can never be ruled out with certainty in practice. In the treatment of hormone-dependent tumors, this invention proves superior to the sole use of antigestagen.

BRIEF DESCRIPTION OF THE DRAWING

Various other objects, features and attendant advantages of the present invention will be more fully appreciated as the same becomes better understood when considered in connection with the accompanying drawing, in which like reference characters designate the same or similar parts throughout the several views, and wherein.

dpc=day post coitus

/d s.c.=per day subcutaneously

/d p.o.=per day by mouth

Figure 1:
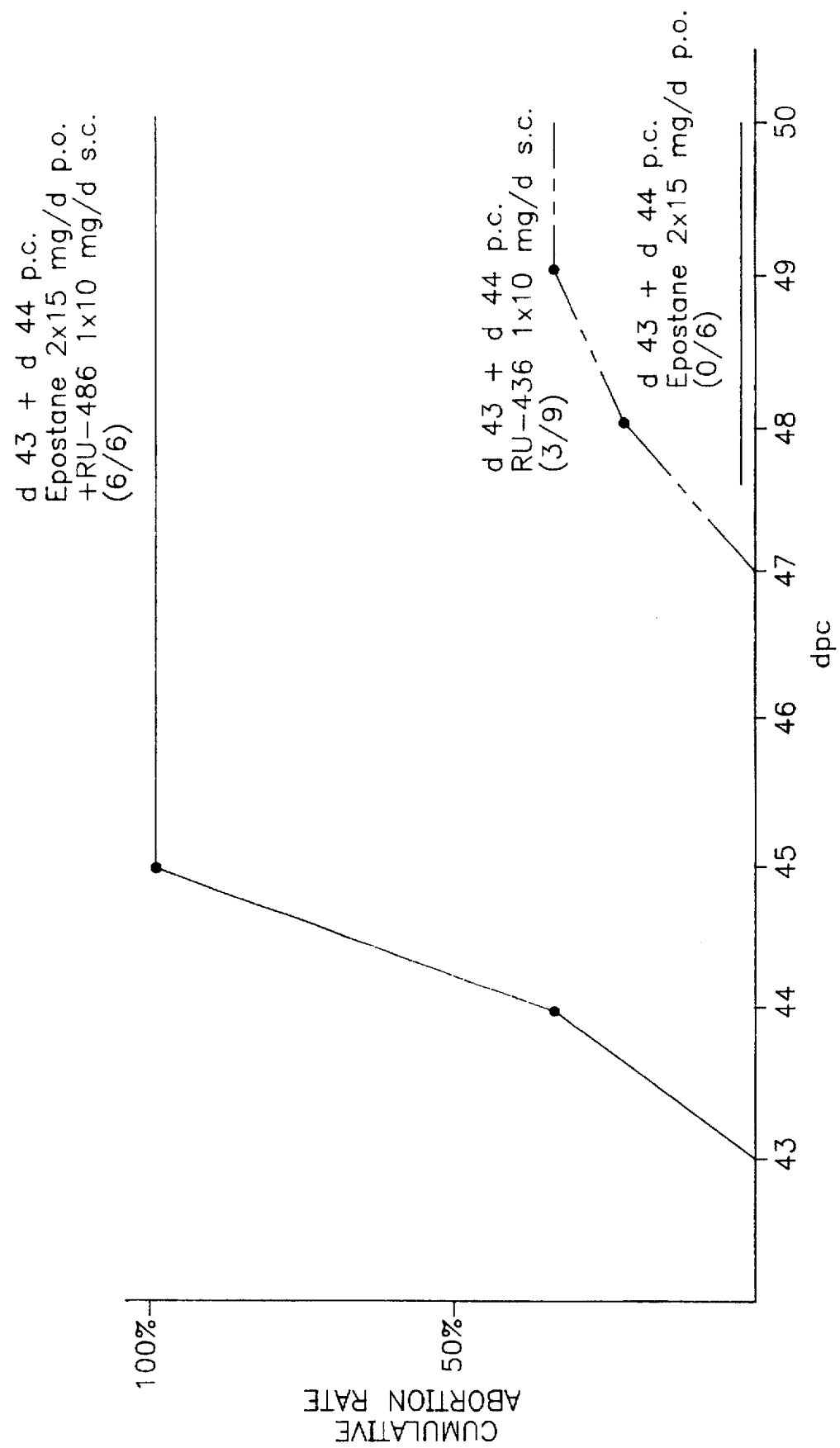
FIG. 1 shows a comparison of the effect of an antigestagen (RU-486) alone, a prostaglandin synthesis inhibitor (epostane) alone, and the combination together in inducing abortion in pregnancy guinea pigs.

Progesterone synthesis inhibitors, preferably of the type of trilostane or epostane, and antigestagens are used for all these purposes in one dose unit or separately, simultaneously and/or sequentially, in a ratio by weight which is essentially 1:40 to 60:1, preferably 1:30 to 30:1. The treatment with progesterone synthesis inhibitors and antigestagens per this invention is, as a rule, carried out for 1 to 4, preferably 1 to 2, days. It is possible and preferred for progesterone synthesis inhibitor and antigestagen to be administered combined in one dose unit.

Suitable antigestagens include all compounds which have a strong affinity for the gestagen receptor (progesterone receptor) and, moreover, have no important intrinsic gestagenic activity. Nonlimiting examples of suitable competitive progesterone antagonists include the following steroids:

11β-[(4-N,N-dimethylamino)-phenyl]-17β-hydroxy-17α-propynyl-4,9(10)-estradien-3-one (RU-486), 11β-[(4-N,N-dimethylamino)-phenyl]-17β-hydroxy-18-methyl-17α-propynyl-4,9(10)-estradien-3-one, and 11β-[(4-N,N-dimethylamino)-phenyl]-17aβ-hydroxy-17aα-propynyl-D-homo-4,9(10),16-estratrien-3-one (European Patent Application 82,400,025.1—Publication No. 0,057,115); and furthermore 11β-p-methoxyphenyl-17β-hydroxy-17α-ethynyl-4,9(10)-estradien-3-one (Steroids 37 (1981), 361–382) and 11β-[(4-N,N-dimethylamino)-phenyl]-17α-hydroxy-17β-(3-hydroxypropyl)-13α-methyl-4,9-gonadien-3-one (European Patent No. 0129 499, corresponding to U.S. Ser. No. 621,308).

The foregoing listing is exemplary only. Many other antigestagens can be used, e.g., as disclosed in *Fertility and Sterility* 40, 253 (1982); *Steroids* 37, 361–382 (1981) and EP 0,057,115.

The amounts of antigestagens used according to the present invention are thereby below the amounts otherwise customary for termination of pregnancy (and, nevertheless, often insufficient for a 100% success rate). In general, 5 to 200 mg of 11β-[(4-N,N-dimethylamino)-phenyl]-17β-hydroxy-17α-propynyl-4,9(10)-estradien-3-one per day (and per dosage unit), or a biologically equivalent amount of another antigestagen, is sufficient. These bioavailably equivalent amounts can be determined routinely and conventionally, e.g., by performing differential potency studies using fully routine pharmacological protocols, e.g., as disclosed in *Fertility and Sterility* 40, 253 (1982); *Steroids* 37, 361 (1981).

Progesterone synthesis inhibitors which can be used according to the invention include but are not limited to all inhibitors of the 3β-hydroxysteroid dehydrogenase enzyme system which reduce the blood progesterone level and are preferably of the type of trilostane (4α,5-epoxy-3,17β-dihydroxy-5α-androst-2-ene-2-carbonitrile) and/or epostane (4α,5-epoxy-3,17β-dihydroxy-4β,17α-dimethyl-5-androst-2-ene-2-carbonitrile).

By compounds of the trilostane and/or epostane type, there are included, among others, 5-androstanes having the structural features: 2-cyano-4α-, 5α-epoxy, and 17β-hydroxy or -alkanoyloxy (1–6 C atoms). See U.S. Pat. No. 4,160,027. In an especially preferred subgenus, there are included such 5α-androstanes which include, instead of a 3-one feature, the structural unit 2-ene-3-hydroxy. In addition, all of such compounds can have substituents, e.g., those defined in U.S. Pat. No. 4,160,027. Suitable progesterone synthesis inhibitors, other than the preferred types, which are also useful for the methods of this invention are well known to those of skill in the art, and include, but are not limited to, the progesterone synthesis inhibitors disclosed in U.S. Pat. No. 4,670,426, as mentioned above.

The amounts of these progesterone synthesis inhibitors which are used are also far below the amounts otherwise customary for the mentioned indications. When epostane is used as the progesterone synthesis inhibitor, as a rule a total of 5–600 mg, preferably 30–300 mg, will suffice. One dose unit contains about 5–300 mg of epostane or a biologically equivalent amount of another such progesterone synthesis inhibitor. These bioavailably equivalent amounts can be determined routinely and conventionally, e.g., by performing differential potency studies using fully routine pharmacological protocols, e.g., as disclosed in Am. J. Obstet. Gynecol., Suppl., 1987, 157, 1065–74. The activity of the claimed combination in treating hormone-dependent tumors can be determined according to already known methods, e.g., as disclosed in the mentioned reference to Maudelonde et al.

The amounts of antigestagen and progesterone synthesis inhibitor can vary from 1:20 to 20:1 when treating a hormone-dependent tumor or treating endometriosis (daily dosage unit 10 to 200 mg of each) or from 1:30 to 30:1 when treating dysmenorrhea (daily dosage unit 10 to 300 mg of each). In every case the upper limit of the dosage depends of the constitution of the respective patient and of the intended duration of the respective treatment.

The antigestagens and progesterone synthesis in inhibitors can be administered, for example, locally, topically, enterally or parenterally. For the preferred oral administration it is possible to use in particular, tablets, coated tablets, capsules, pills, suspensions or solutions, which can be prepared in the customary manner using the additives and vehicles customary in pharmacy. See, e.g., the several references mentioned above. Preparations suitable for local or topical administration include, for example, vaginal suppositories or transdermal systems such as skin plasters.

According to the present invention for terminating pregnancy or inducing labor the combination is administered in every case after nidation, preferably in the second or third trimester of pregnancy, in the case of inducing labor shortly before or on the term of labor. The compounds can be administered in any sequence, preferably simultaneously, in the case of sequential administration, the second may be administered at any time after the first so long as it becomes bioavailable in the patient at the same time as an effective dose of the first is still bioavailable. For example, the ProI can be administered within 1 or 2 days after AG.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P. 37 20 420.3, are hereby incorporated by reference.

EXAMPLES

Example 1

Composition of a tablet containing 11β-[(4-N,N-dimethylamino)-phenyl]-17β-hydroxy-17α-propynyl-4,9(10)-estradien-3-one for oral administration

| | |
|---|---|
| 10.0 mg | of 11β-[(4-N,N-dimethylamino)-phenyl]-17β-hydroxy-17α-propynyl-4,9(10)-estradien-3-one |
| 140.5 mg | of lactose |
| 69.5 mg | of corn starch |
| 2.5 mg | of polyvinylpyrrolidone 25 |
| 2.0 mg | of Aerosil |
| 0.5 mg | of magnesium stearate |
| 225.0 mg | total weight |

Example 2

Composition of a tablet containing 4α,5-epoxy-3,17β-dihydroxy-4β,17α-dimethyl-5α-androst-2-ene-2-carbonitrile (epostane) for oral administration

| | |
|---|---|
| 30 mg | of 4α,5-epoxy-3,17β-dihydroxy-4β,17α-dimethyl-5α-androst-2-ene-2-carbonitrile |
| 201 mg | of lactose |
| 139 mg | of corn starch |
| 5.0 mg | of polyvinylpyrrolidone 25 |
| 4.0 mg | of Aerosil |
| 1.0 mg | of magnesium stearate |
| 380.0 mg | total weight |

Example 3

Composition of a tablet containing 4α,5-epoxy-3,17β-dihydroxy-5α-androst-2-ene-2-carbonitrile (trilostane) for oral administration

| | |
|---|---|
| 20.0 mg | of 4α,5-epoxy-3,17β-dihydroxy-5α-androst-2-ene-2-carbonitrile |
| 281.0 mg | of lactose |
| 139.0 mg | of corn starch |
| 5.0 mg | of polyvinylpyrrolidone 25 |
| 4.0 mg | of Aerosil |
| 1.0 mg | of magnesium stearate |
| 450.0 mg | total weight |

Pharmacological findings

The model substances selected for experiments on pregnancy guinea pigs were the progesterone synthesis inhibitor epostane and the antigestagen 11β-[(4-N,N-dimethylamino)-phenyl]-17β-hydroxy-17α-propynyl-4,9(10)-estradien-3-one (RU 486). The dosages tested are shown in the figure.

Investigations on pregnant guinea pigs
Test of the combination Description of the experiment Pregnant guinea pigs weighing about 800 g were entered in the experiment on day 42 of pregnancy (the 2nd day of vaginal opening in the mating period was regarded as the first day of pregnancy). Pregnancy was checked by palpation before the start of the experiment. The treatment with the selected test substances and the combination was effected by oral (epostane) or subcutaneous (RU 486) administration each day on days 43 and 44 of pregnancy. For this purpose, the antigestagen was dissolved in benzyl benzoate+castor oil (mixing ratio 2+4.5), and the daily dose was injected s.c. in a volume of 1.0 ml. The daily dose of epostane was suspended as microcrystals in Myrj®/saline solution and administered divided into two equal doses in the morning and afternoon. Any expulsion of embryos was checked several times a day during and after the treatment. The animals were sacrificed on day 50 of pregnancy. The uteri were inspected, and the fetuses were examined.

Results

The results of the experiments on the induction of abortion in pregnant guinea pigs on combined administration of antigestagens and progesterone synthesis inhibitors are shown in the figure.

Progesterone synthesis inhibitors

At an oral dose of 30.0 mg/day, epostane was totally inactive in terms of an abortive effect (see FIG. 1).

Antigestagens

With the antigestagen RU 486 an existent pregnancy was terminated with 10 mg/d s.c. in 3 of 9 treated animals. The abortions took place after a latency period of 4 to 6 days after the start of treatment (see FIG. 1).

Antigestagen/progesterone synthesis inhibitor combination

The combination of marginally effective antigestagen doses (10.0 mg of RU 486/d s.c.) with an ineffective epostane dose of 30 mg/d orally resulted in an abortion rate of 100% and a far more rapid occurrence of the abortions. The latency period was shortened to a maximum of 2 days (see FIG. 1).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical combination comprising effective amounts of a progesterone synthesis inhibitor of formula I

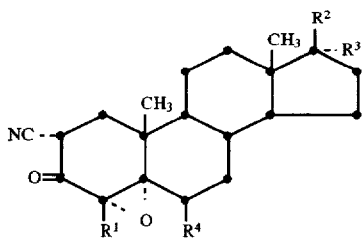

or, of formula II

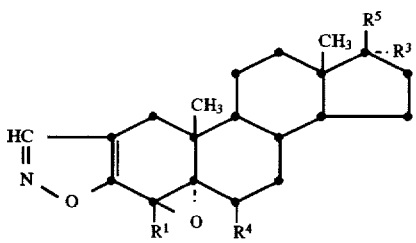

wherein
$R^1$ is H or methyl;
$R^2$ is hydroxy or $C_{1-6}$-alkanoyloxy:
$R^3$ is H, $C_{1-3}$-alkyl, -alkenyl or -alkynyl, or $R^2$ and $R^3$ together are oxo or ethylenedioxy;
$R^4$ is H or methyl;
$R^5$ is hydroxy;
or 3-enol $C_{1-3}$-alkanoate esters thereof;
with the proviso that when $R^1$ is H, $R^4$ is α-methyl, and when $R^1$ is methyl, $R^4$ is H or β-methyl;
and an antigestagen.

2. A pharmaceutical combination of claim 1, wherein the progesterone synthesis inhibitor is trilostane.

3. A pharmaceutical combination of claim 1, wherein the progesterone synthesis inhibitor is epostane.

4. A pharmaceutical combination of claim 1, wherein the progesterone synthesis inhibitor and the antigestagen are in a ratio by weight of 1:40 to 60:1, respectively.

5. A pharmaceutical combination of claim 1, wherein the progesterone synthesis inhibitor and antigestagen are in a common dose unit.

6. A pharmaceutical combination of claim 1, wherein the progesterone synthesis inhibitor dose unit contains 5 to 600 mg of epostane or a biologically equivalent amount of another progesterone synthesis inhibitor of the epostane or trilostane type.

7. A pharmaceutical combination of claim 6, wherein the antigestagen dose unit contains 5 to 200 mg of 11β-[(4-N, N-dimethylamino)-phenyl]-17β-hydroxy-17α-propynyl-4,9 (10)-estradien-3-one or a biologically equivalent amount of another antigestagen.

8. A pharmaceutical combination of claim 7, wherein the progesterone synthesis inhibitor and the antigestagen are in a ratio by weight of 1:40 to 60:1, respectively.

9. A pharmaceutical combination of claim 8, wherein the antigestagen is 11β-[(4-N,N-dimethylamino)-phenyl]-17β-hydroxy-17α-propynyl-4,9(10)-estradien-3-one and the progesterone synthesis inhibitor is trilostane or epostane.

10. A pharmaceutical combination of claim 1, wherein the antigestagen dose unit contains 5 to 200 mg of 11β-[(4-N, N-dimethylamino)-phenyl]-17β-hydroxy-17α-propynyl-4,9 (10)-estradien-3-one or a biologically equivalent amount of another antigestagen.

11. A method of inducing labor after nidation, terminating pregnancy after nidation, treating a hormone-dependent tumor, treating endometriosis, or treating dysmenorrhea, comprising administering a combination of claim 1.

12. A method of claim 11, wherein said administration is for the purpose of inducing labor.

13. A method of claim 11, wherein said administration is for the purpose of terminating a normal or pathological pregnancy.

14. A method of claim 11, wherein said administration is for the purpose of treating endometriosis or dysmenorrhea.

15. A method of claim 11, wherein said progesterone synthesis inhibitor and antigestagen are administered separately and sequentially.

16. A method of claim 15, wherein the first administered of either the progesterone synthesis inhibitor or the antigestagen, which are separately and sequentially administered, is bioavailable when the second is administered.

17. A method of claim 11, wherein said progesterone synthesis inhibitor and antigestagen are administered separately and simultaneously.

18. A method of claim 17, wherein said progesterone synthesis inhibitor and antigestagen are administered in the same dose unit.

19. A method of claim 11, whereby the amounts of progesterone synthesis inhibitor and antigestagen are each ineffective or marginally effective, but when coadministered, provide a synergistic effect.

20. A composition of claim 1, wherein the amounts of progesterone synthesis inhibitor and antigestagen are each ineffective or marginally effective, but when coadministered, provide a synergistic effect.

21. A method of inducing labor after nidation, terminating pregnancy after nidation, treating a hormone-dependent tumor, treating endometriosis, or treating dysmenorrhea, comprising administering a combination comprising effective amounts of a progesterone synthesis inhibitor and an antigestagen.

22. A method of claim 21, wherein said administration is for the purpose of inducing labor.

23. A method of claim 21, wherein said administration is for the purpose of terminating a normal or pathological pregnancy.

24. A method of claim 21, wherein said administration is for the purpose of treating endometriosis or dysmenorrhea.

25. A method of claim 21, wherein said progesterone synthesis inhibitor and antigestagen are administered separately and sequentially.

26. A method of claim 25, wherein the first administered of either the progesterone synthesis inhibitor or the antigestagen, which are separately and sequentially administered, is bioavailable when the second is administered.

27. A method of claim 21, wherein said progesterone synthesis inhibitor and antigestagen are administered separately and simultaneously.

28. A method of claim 21, wherein said progesterone synthesis inhibitor and antigestagen are administered in the same dose unit.

29. A method of claim 21, wherein the progesterone synthesis inhibitor is epostane or trilostane.

30. A method of claim 21, wherein the progesterone synthesis inhibitor is aminogluthetimide, 2α-cyano-4,4, 17α-trimethyl-5-androst-5-ene-17β-ol-3-one, or 20,25-diazacholesterol.

31. A method of claim 21, whereby the amounts of progesterone synthesis inhibitor and antigestagen are each ineffective or marginally effective, but when coadministered, provide a synergistic effect.

* * * * *